United States Patent
Sitnik

(10) Patent No.: US 11,040,510 B2
(45) Date of Patent: Jun. 22, 2021

(54) ROSIN PRESS SYSTEM

(71) Applicant: Spencer Sitnik, Downey, CA (US)

(72) Inventor: Spencer Sitnik, Downey, CA (US)

(*) Notice: Subject to any disclaimer, the term of this patent is extended or adjusted under 35 U.S.C. 154(b) by 458 days.

(21) Appl. No.: 15/917,214

(22) Filed: Mar. 9, 2018

(65) Prior Publication Data

US 2018/0257326 A1    Sep. 13, 2018

Related U.S. Application Data

(60) Provisional application No. 62/469,688, filed on Mar. 10, 2017, provisional application No. 62/528,962, filed on Jul. 5, 2017.

(51) Int. Cl.
*B30B 9/04* (2006.01)
*B30B 15/34* (2006.01)
*B30B 15/06* (2006.01)
*B30B 1/08* (2006.01)

(52) U.S. Cl.
CPC .......... *B30B 15/064* (2013.01); *B30B 1/08* (2013.01); *B30B 9/04* (2013.01); *B30B 15/065* (2013.01); *B30B 15/34* (2013.01); *A61K 2236/31* (2013.01); *A61K 2236/37* (2013.01)

(58) Field of Classification Search
CPC .... C11B 1/06; C11B 1/08; B30B 9/02; B30B 9/04; B30B 9/06; B30B 15/00; B30B 15/02; B30B 15/062; B30B 15/064; B30B 15/065

See application file for complete search history.

(56) References Cited

U.S. PATENT DOCUMENTS

| | | | | |
|---|---|---|---|---|
| 1,454,721 A | * | 5/1923 | Bickel | B30B 9/04 100/218 |
| 5,152,454 A | * | 10/1992 | Warta | B65D 85/78 229/4.5 |
| 5,291,999 A | * | 3/1994 | Phair | A47G 33/045 206/423 |
| 5,885,625 A | * | 3/1999 | Beane | B22F 3/004 264/109 |
| 7,972,517 B1 | * | 7/2011 | Miller | C02F 11/14 210/710 |
| 8,459,086 B2 | * | 6/2013 | Vigurs | B21C 37/0815 72/367.1 |
| 10,196,582 B1 | * | 2/2019 | Black | C11B 1/08 |
| 2009/0293742 A1 | * | 12/2009 | Murphy | B01D 29/27 100/215 |
| 2010/0147937 A1 | * | 6/2010 | Reid | B65D 81/3876 229/403 |

(Continued)

FOREIGN PATENT DOCUMENTS

| | | | | | |
|---|---|---|---|---|---|
| DE | 807661 C | * | 7/1951 | | B30B 15/00 |
| EP | 3180994 A2 | * | 6/2017 | | A23B 7/024 |
| GB | 158844 A | * | 5/1922 | | B01D 29/6438 |

*Primary Examiner* — Shelley M Self
*Assistant Examiner* — Jared O Brown
(74) *Attorney, Agent, or Firm* — Risso I.P.

(57) ABSTRACT

Described is a rosin press system for extract rosin (oil) from plant material. The rosin press system includes a cone-shaped male plate and a cone-shaped female plate formed to matingly receive the cone-shaped male plate. The plates can be heated such that when plant material is pressed between the plates, rosin is pressed from the plant material and allowed to drain from a drain hole positioned at the bottom of the cone-shaped female plate.

1 Claim, 19 Drawing Sheets

(56) References Cited

U.S. PATENT DOCUMENTS

| | | | |
|---|---|---|---|
| 2012/0055941 A1* | 3/2012 | Messerschmid | B67C 11/00 220/694 |
| 2016/0296464 A1* | 10/2016 | Lindsay | A61K 9/009 |
| 2017/0305094 A1* | 10/2017 | Kosse | B30B 1/14 |
| 2018/0008655 A1* | 1/2018 | Weikel | A61K 36/185 |
| 2018/0178473 A1* | 6/2018 | Perez | B30B 9/06 |
| 2018/0250903 A1* | 9/2018 | Yan | F16P 3/22 |

\* cited by examiner

US 11,040,510 B2

ROSIN PRESS SYSTEM

CROSS-REFERENCE TO RELATED APPLICATIONS

This is a non-provisional application of U.S. Provisional Application No. 62/469,688, filed on Mar. 10, 2017, the entirety of which is incorporated herein by reference.

This is a non-provisional application of U.S. Provisional Application No. 62/528,962, filed on Jul. 5, 2017, the entirety of which is incorporated herein by reference.

BACKGROUND OF THE INVENTION

(1) Field of Invention

The present invention relates to a plant material/oil extractor and, more particularly, to a rosin press for extracting rosin toil) from plant material.

(2) Description of Related Art

Rosin is an extraction process that uses both heat and pressure to squeeze an extract (e.g., oil, resin, or rosin) from plant material. The extraction process typically uses a rosin press that includes flat heat plates that are pressed together to squeeze/press the extract from the plant material. A problem with existing systems is that they are limited in their footprint in which they can extract rosin. In other words, the area of the plates limits the size of the heat plates. Further, the very nature of existing heat plates makes it difficult to accumulate or otherwise collect the extracted rosin.

Thus, a continuing need exists for a rosin press that improves upon the deficiencies of the prior art and expands the previously limited size of the heated plates.

SUMMARY OF INVENTION

The present invention relates to a plant material/oil extractor and, more particularly, to a rosin press. The rosin press includes both a male plate (e.g., cone-shaped) and a female plate with a recess (e.g., cone-shaped female plate, etc.) formed to matingly receive the cone-shaped male plate.

In another aspect, at least one of the cone-shaped male plate and female plate are heated with one or more heating elements.

In another aspect, the female plate has a centrally positioned drain hole.

In yet another aspect, the male plate includes a stem rising from the male plate.

In another aspect, the rosin press further comprises a base supporting the female plate; a riser attached with the base; a pair of rocker arms pivotally attached with the riser about a pivot point, the rocker arms having a ram bolt hole and a stem bolt hole, wherein the stem of the male plate is pivotally connected with the stem bolt hole; and a ram attached with the base, the ram having a ram arm connected with the ram bolt hole, whereby causing the ram arm to raise forces the pair of rocker arms to pivot about the pivot point and press the male plate into the female plate.

In another aspect, the rosin press system also includes a parchment cone, the parchment cone formed of planar parchment paper having at least two cut lines therein, such that upon rolling and affixing the cut lines, the parchment paper is maintained as a parchment cone.

In yet another aspect, a mesh bag is included, the mesh bag having a truncated cone shape. The mesh bag includes an open top portion and an open bottom portion, with the top portion being wider than the bottom portion, and further comprising a flap extending from the open top portion.

In yet another aspect, an O-ring is also positioned within the cone-shaped female plate.

In another aspect, the rosin press system also includes a flat male plate having a stem protruding therefrom, the flat male plate being interchangeable with the cone-shaped male plate.

In yet another aspect, the rosin press system also includes a flat female plate, the flat female plate being formed to nest within a top portion of the cone-shaped female plate.

Additionally, a puck mould is included.

In yet another aspect, a plurality of magnets are attached with a top portion of the cone-shaped female plate.

Further, the cone-shaped male plate has a truncated tip.

Additionally, the cone-shaped male plate is pressed into the cone-shaped female shape, a gap exists between the cone-shaped male and female plates proximate the drain hole.

Finally, as can be appreciated by one in the art, the present invention also comprises a method for forming and using the rosin press described herein.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention relates to a plant material/oil extractor and, more particularly, to a rosin press for extracting rosin (oil) from plant material. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter clockwise have been used for convenience purposes only and are not intended to imply any particular fixed direction. Instead, they are used to reflect relative locations and/or directions between various portions of an object.

(1) Description

Figure 1:
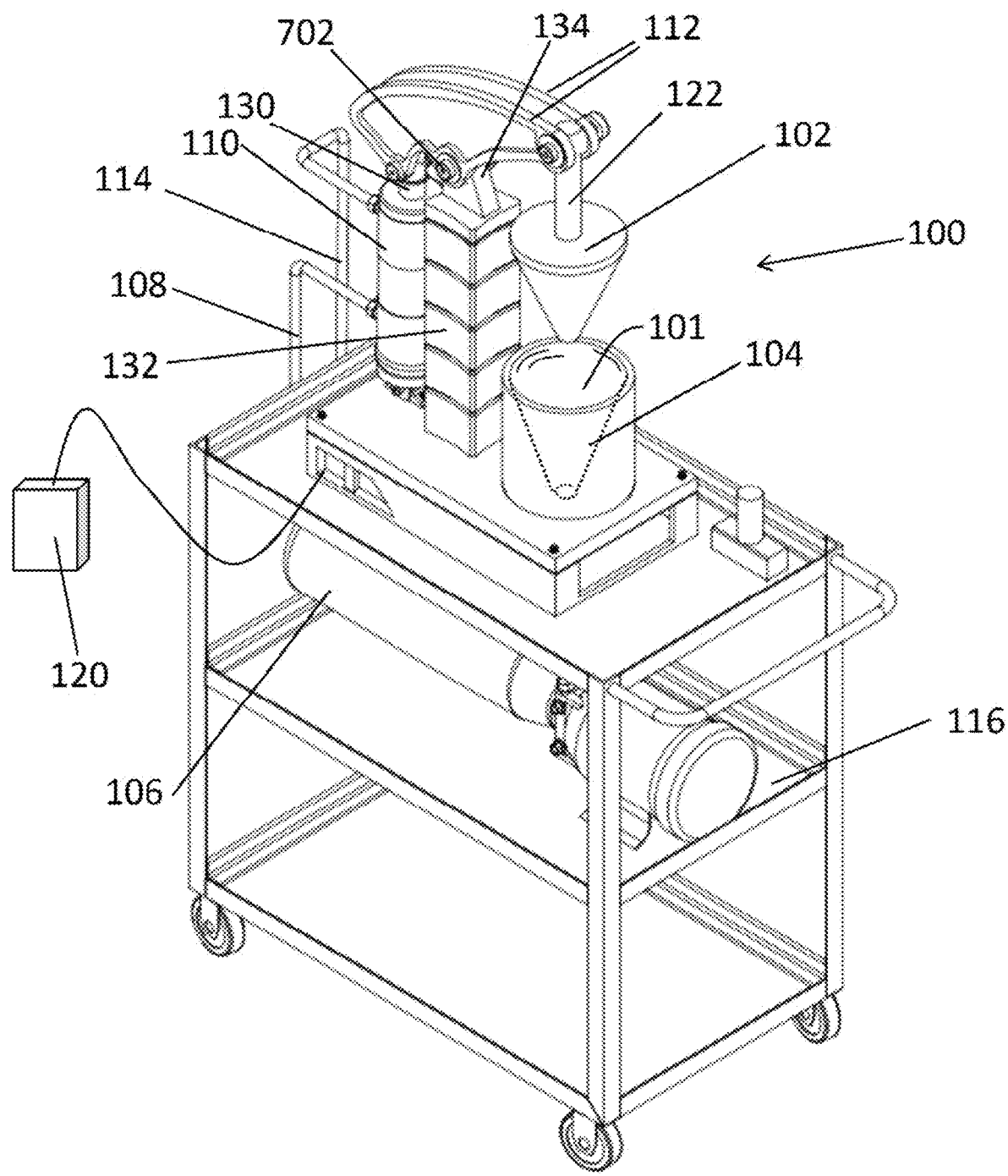
FIG. 1 is an illustration of a rosin press according to various embodiments of the present invention, depicting the rosin press with male and female cone-shaped plates and being in an open or ready position.
Figure 12:
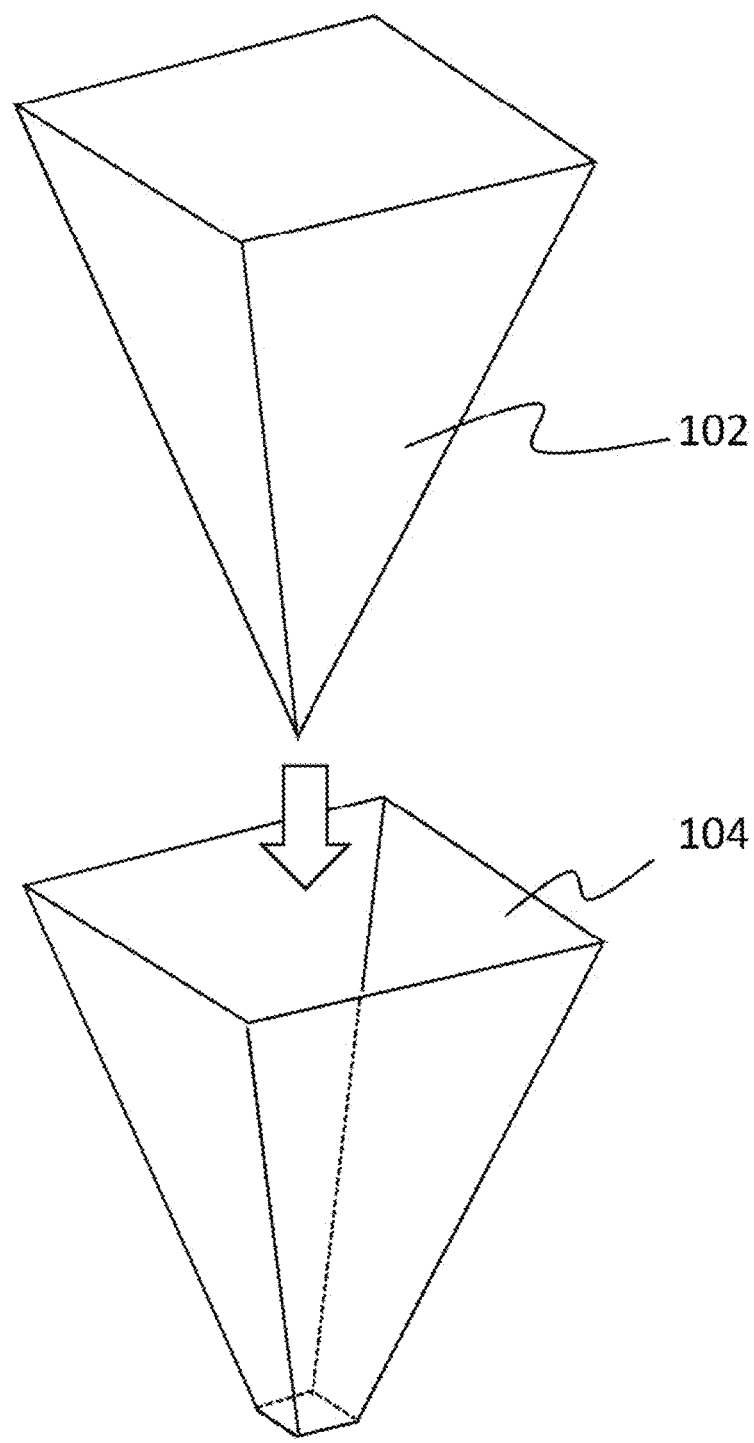
FIG. 12 is an illustration depicting matingly engaging male and female plates according to various embodiments of the present invention.

As noted above and as shown in the figures, this disclosure is directed to a rosin press. As shown in FIG. 1, the rosin press 100 is an extraction device that uses heat and pressure to provide a precise pressure for pressing oils and/or rosin from plant materials. The plant material that may be used with the rosin press 100 is any desirable plant material from which rosin (oil) can be extracted through pressure and/or heat. Notably, the press 100 includes at least two plates, a male plate 102 and a female plate 104 (e.g., plastic plates or metal plates, such as aluminum, or other suitable materials). Although not limited thereto, in various embodiments, the male plate 102 is suspended from a rocker arm 112 using a plate stem 122. Each of the plates 102 and 104 can be formed in any suitable shape to allow for mating engagement between the two plates and an ability to press the plant material therebetween. In other words, the female plate 104 is formed with a recess 101 to matingly receive the male plate 102. Desirably, each of the plates are formed as matingly engaging cone shapes. However, it should be understood that although the rosin press is described as having cone-shaped plates, the invention is not intended to be limited thereto as the features described herein can also be equally applied to any matingly engaging plate shapes. For example, FIG. 12 illustrates a pyramid-shaped male 102 and female plate 104. Although the plates 102 and 104 are depicted as a four-sided period in FIG. 12, it should be understood that the plates can be formed to include any desired number of sides, such a seven-sided period, etc. Another example would include a dome-shaped male plate and a corresponding bowl-shaped female plate.

However, for illustrative purposes, the plates are described and illustrated as cone-shaped plates. During operation, the cone-shaped male plate 102 is pressed into a female plate 104 that is also conically shaped and formed to receive the male plate 102. Although the term male or female plate may be used herein, it should be understood that the term also includes the relevant shape, such as cone-shape, funnel-shape, etc. Further, while the cone-shaped female plate 104 is described as having a cone shape, the inverted shape formed as a recess can also be interchangeably referred to as a funnel-shape.

Figure 2:
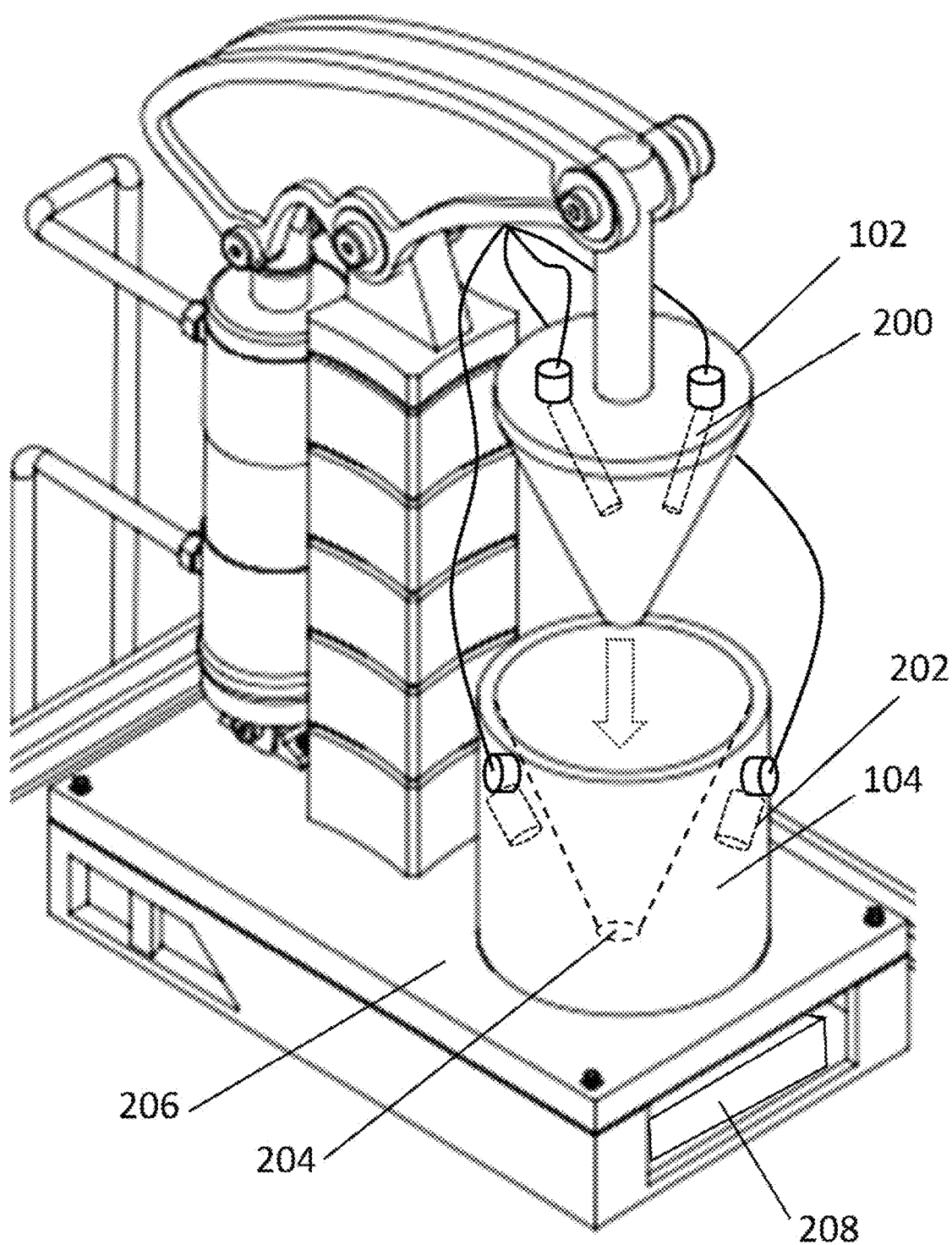
FIG. 2 is an illustration of the rosin press, depicting a drain hole and heating elements placed on and inside the plates.

There are several benefits to the cone-shaped plates 102 and 104. For example, the cone-shaped plates 102 and 104 allow for an increased surface area of even pressure distribution for pressing rosin from the plant material and subsequent filtration through a mesh bag (e.g., micron mesh bag) as described in further detail below. Further, when rosin is pressed from plant material that is positioned between the plates 102 and 104, the downward angled configuration of the plates 102 and 104 allow for the rosin/oil to escape from plant material out of the mesh bag (e.g., micron mesh bag as described below) and down the heated plates 102 and 104 out of a drain hole (depicted as element 204 in FIG. 2) at the bottom of the female plate 104.

The two plates 102 and 104 are pressed together using any suitable mechanism or device that provides sufficient pressure and/or heat to press the rosin from the plant material. As a non-limiting example, the rosin press 100 includes a hydraulic ram 110 (or electric actuator in other aspects) connected to one or more rocker arms 112 that drive the plates 102 and 104 together. The rosin press 100 includes any components as may be necessary to perform the operations described herein and to selectively operate the hydraulic ram 110. As a non-limiting example, a battery or other power source can be used to power a hydraulic pump 106 that, operates the ram 110. There is a controller 120 (e.g. remote control, wired, wireless, hard wired, etc.) connected to the rosin press 100 that is configured to operate the rosin press 100. The controller 120 includes any desirable control features as may be needed to press the extract from the plant material. In various embodiments, the controller 120 is hand held, with an extension cord for uses over longer distances (e.g., a 15' cord) or may be wirelessly controlled using any suitable technology, such as a Bluetooth application via an iPhone or any smart phone. As a non-limiting example, pressing an "up" button on the controller 120 (e.g., remote control) will activate a hydraulic pump relay solenoid or electronic trigger to cause the pump 106 to push vegetable oil, or another functional oil, up through the supply line 108 and into the ram 110, eventually flowing out through the return hose 114. The ram 110, which ideally can achieve 2500 psi (or any other desired pressure), then fills with oil and pulls down a ram arm 130, allowing a rocker arm 112 to pivot at a pivot point 702 to lift the cone-shaped male plate 102 from the corresponding cone-shaped female plate 104. Alternatively, pressing "down" on the remote 120 will activate the hydraulic pump relay solenoid or electronic trigger to cause the pump 106 to send vegetable oil into the bottom portion of the ram 110, which will push up on the rocker arm 112, which in turn forces the cone-shaped male plate 102 into the cone-shaped female plate 104 using leverage from the rocker arm 112, thereby allowing as much force as possible from the male plate 102 to penetrate the female plate 104 with maximum force. In doing so, extract (e.g., oil, resin or rosin) is pressed from plant material positioned within the female plate 104. In various embodiments and due to the design of the rocker arm 112 (as is discussed below), the rocker arm is able to generate approximately 14,000 lbs. of force to the plates 102 and 104.

To assist the extract (e.g., rosin) in being extracted/pressed from the plant material and flowing from the plates 102 and 104, heating elements are desirably included in one or both of the plates 102 and 104. The male 102 and female 104 plates can be formed to include heating elements using any suitable mechanism, device or technique. As a non-limiting example and illustrated in FIG. 2, the male 102 and female 104 cone-shaped plates are operated by two digital heating controllers for dual heating accuracy. An example of the digital heating controllers includes the MYPIN T series controller as produced by MYPIN Electrical Co., Ltd, located at Floor 1, No. 7, Lane 5, Anhe St., Fengyu Rd., Bogong Community, Dongfeng Town, Zhongshan, Guangdong, China.

Further, there are desirably two heating elements per male plate 102 and female plate 104, each of which is connected with the necessary power (e.g., battery, hardwire, etc.) and circuitry as needed for control. For example, the male plate heating elements 200 are positioned into holes drilled into the center of the male plate 102, and the female plate heating elements 202 are positioned into holes drilled onto the sides of the female plate 104. The use of two heating elements in each plate assists in maintaining a constant temperature around each plate. Both signal the temperature to the MYPIN controller through corresponding temperature probes to control the plates 102 and 104 at the desired temperature. The temperature can be set to any desired temperature. As a non-limiting example, it is desirable to have the male plate 102 set between 120 degrees and 240 degrees Fahrenheit and the female plate set between 120 degrees and 240 degrees Fahrenheit, depending on oil type or plant material. The female plate 104 can also be formed to include a fiberglass heat shield for safety and efficiency purposes.

Due to the unique cone-shaped plates 102 and 104, the rosin press 100 gains the correct amount of pressure needed to properly press the size of surface area that is desired to be pressed due leverage from the rocker arm. The pump can be desirably controlled to allow for electric "speed" control with the remote and "up" and "down" features as described above without the use of an added spring. In other embodiments and depending on the features of the particular pump selected, a spring may be needed to raise the male plate. In other embodiments, the hydraulic pump 106 should desirably have a key activated battery option for safety purposes, so that a key must be inserted into the system to allow operation of the hydraulic or pneumatic parts.

Further, through the addition of heat and as noted above, the heated male 102 and female 104 plates allow the flow of resin/oil to be controlled with gravity directional flow (with a gap between the meeting of the plates proximate the drain hole), after being separated from plant material from the heat by the plates. In other words, because the female plate 104 is a heated and an inverted cone-shape, extracted material can easily flow down the cone-shape to the centrally positioned drain hole 204. An O-ring (described in further detail below) can be added to control the directional flow of the rosin (oil) to flow according to gravity where the plant material provides a gap point for the oil to flow. This provides for a better flow of rosin or oil in a controlled manner that drains from the female plate 104 via the drain hole 204. Further, the female plate rests atop a base 206 which allows for placement of a tray or drawer beneath the female plate 104 for catching all of the draining rosin. The base 206 may simply be a frame or may also have a base hole that allows for alignment of the drain hole 204 to allow for the rosin to fall from the female plate 104 into the tray or drawer 208. In some aspects and as shown, the base 206 includes a top and bottom base plate. In various embodiments, the top base plate secures the female cone-shaped plate 104 and the bottom base plate secures the tray or drawer 208 to catch the rosin. In other aspects, there can be a second tray 116 or drawer as seen in FIG. 1, which can be used for holding tools on a mobile cart or other stand.

Figure 3:
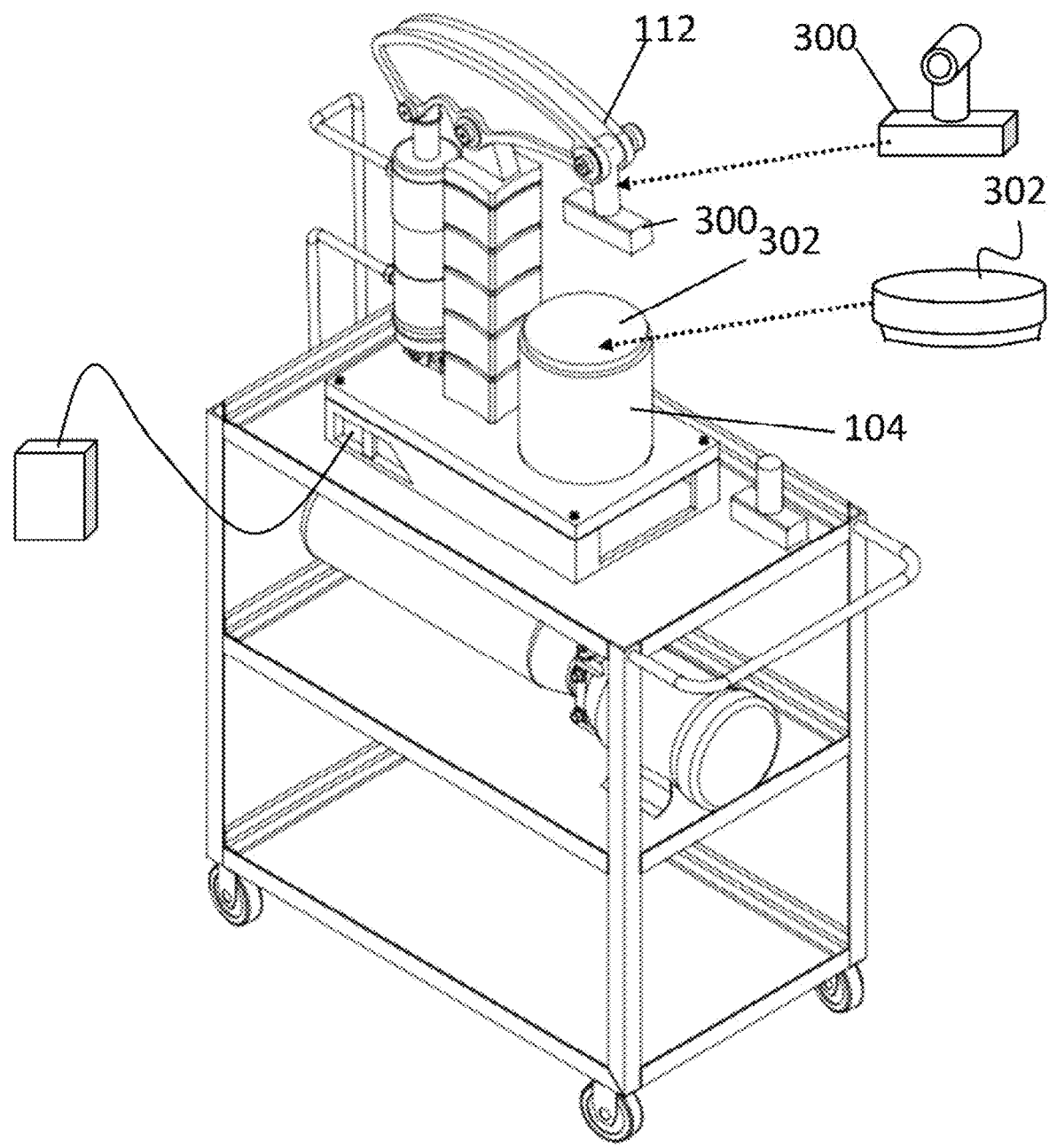
FIG. 3 is an illustration of the rosin press according to various embodiments of the present invention, depicting flat plates designed for smaller quantities of plant material.

It should be understood that while the cone-shaped male 102 and female 104 plates allow for the maximum amount of plant material to be processed and pressed (due to the conically shaped surface area), it is also possible to substitute the plates for smaller plates to process smaller amounts of plant material, or lager plates to process larger amounts, or multiple plates to prepare multiple plates for rosin pressing at one time. This aspect can be seen in FIG. 3, which depicts another option of differently sized plates. In this aspect, the plates are interchangeable with any desired plate. For example, a smaller and flat male plate 300 can simply be bolted to the rocker 112 after removing the cone-shaped male plate 102. Further, the flat female plate 302 can be formed to nest (e.g., via protrusion on a bottom side) on top of the cone-shaped female plate 104 and provide a flat top.

Figure 4:
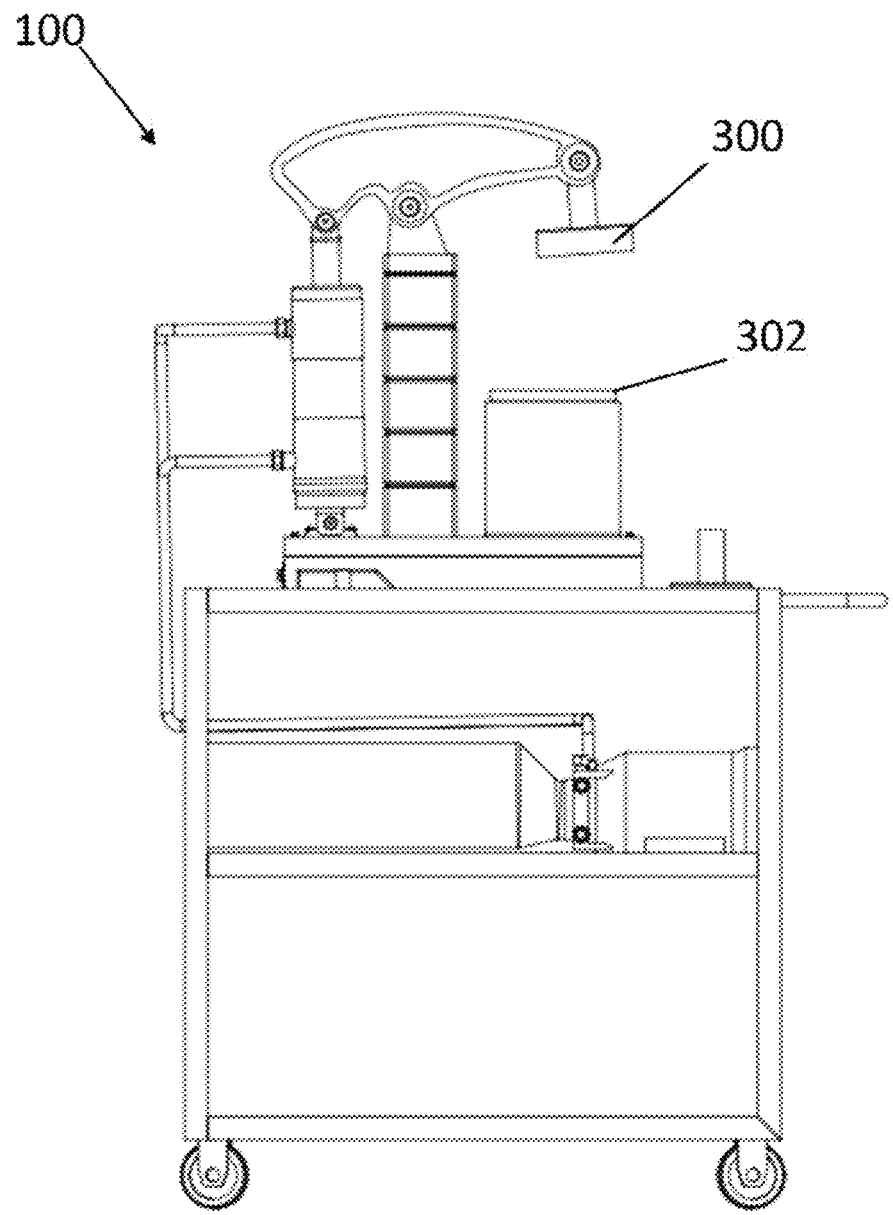
FIG. 4 is a side-view illustration of the rosin press as depicted in FIG. 3.
Figure 5:
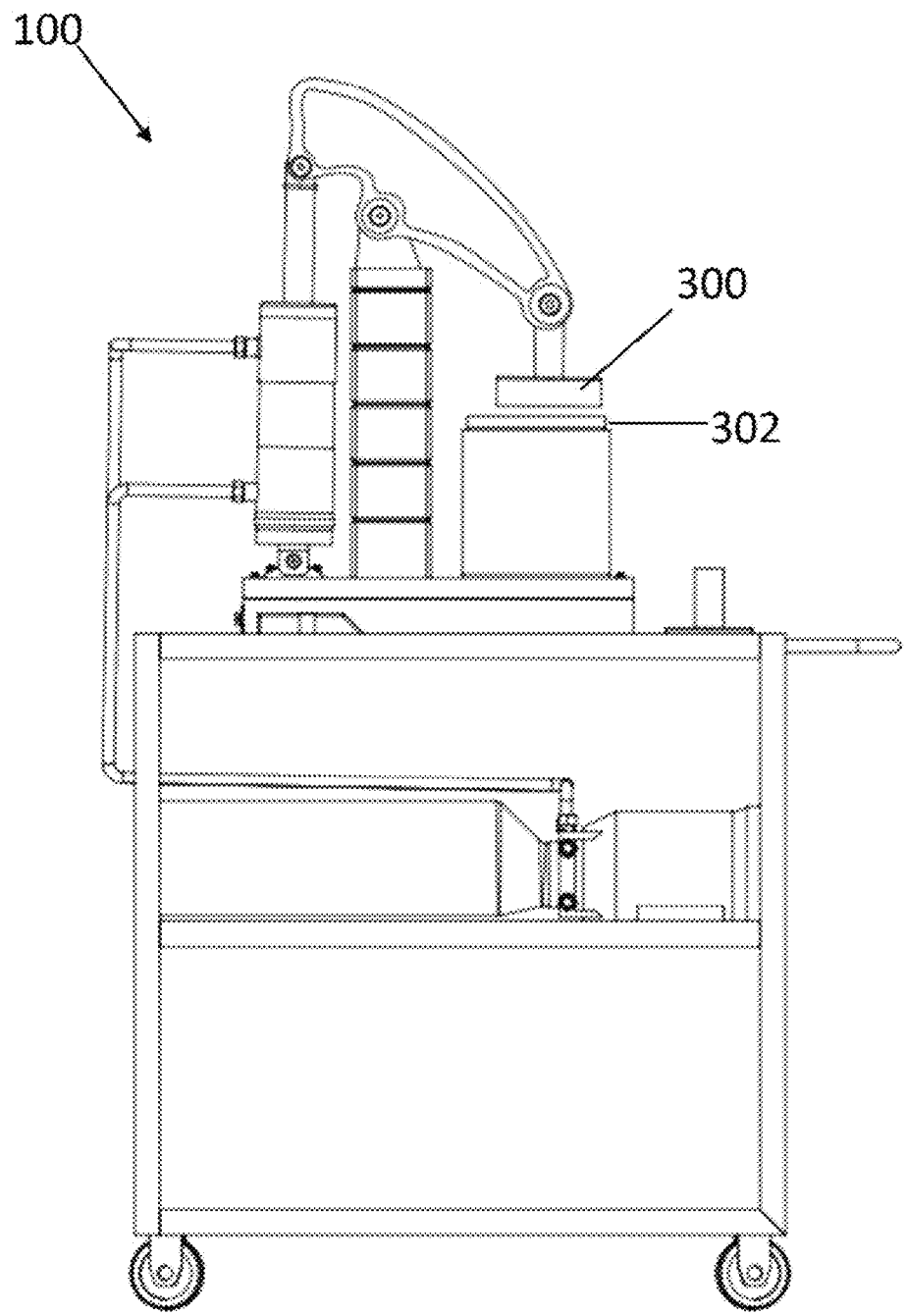
FIG. 5 is a side-view illustration of the rosin press, depicting the press as shown in FIG. 3 in a closed or press position.

This substitution would not have to change the previously mentioned components, as the plates would simply be changed out. The rosin press configuration can be seen in greater detail in the side-view illustrations of FIGS. 4 and 5. Specifically, FIGS. 4 and 5 are side-view illustrations of the rosin press 100, showing the flat male 300 and flat female plates 302 in open and closed positions, respectively.

As can be appreciated by those skilled in the art, there are several additional features included in the rosin press 100 that are described herein. In various embodiments, the rosin press 100 includes all of the relevant hardware and/or components as may be necessary to implement the features and functions as described herein. Further, while specific examples are provided, it should be understood that the invention is not limited thereto and that other components can be used to provide similar functionality as understood by those skilled in the art. For example and n various embodiments, all components of the rosin press 100 can be formed to fit within a transportable storage container with wheels, etc. Further, various embodiments of the rosin press 100 include hydraulic quick connect lines to allow a user to easily attach/detach the hydraulic lines.

Figure 6:
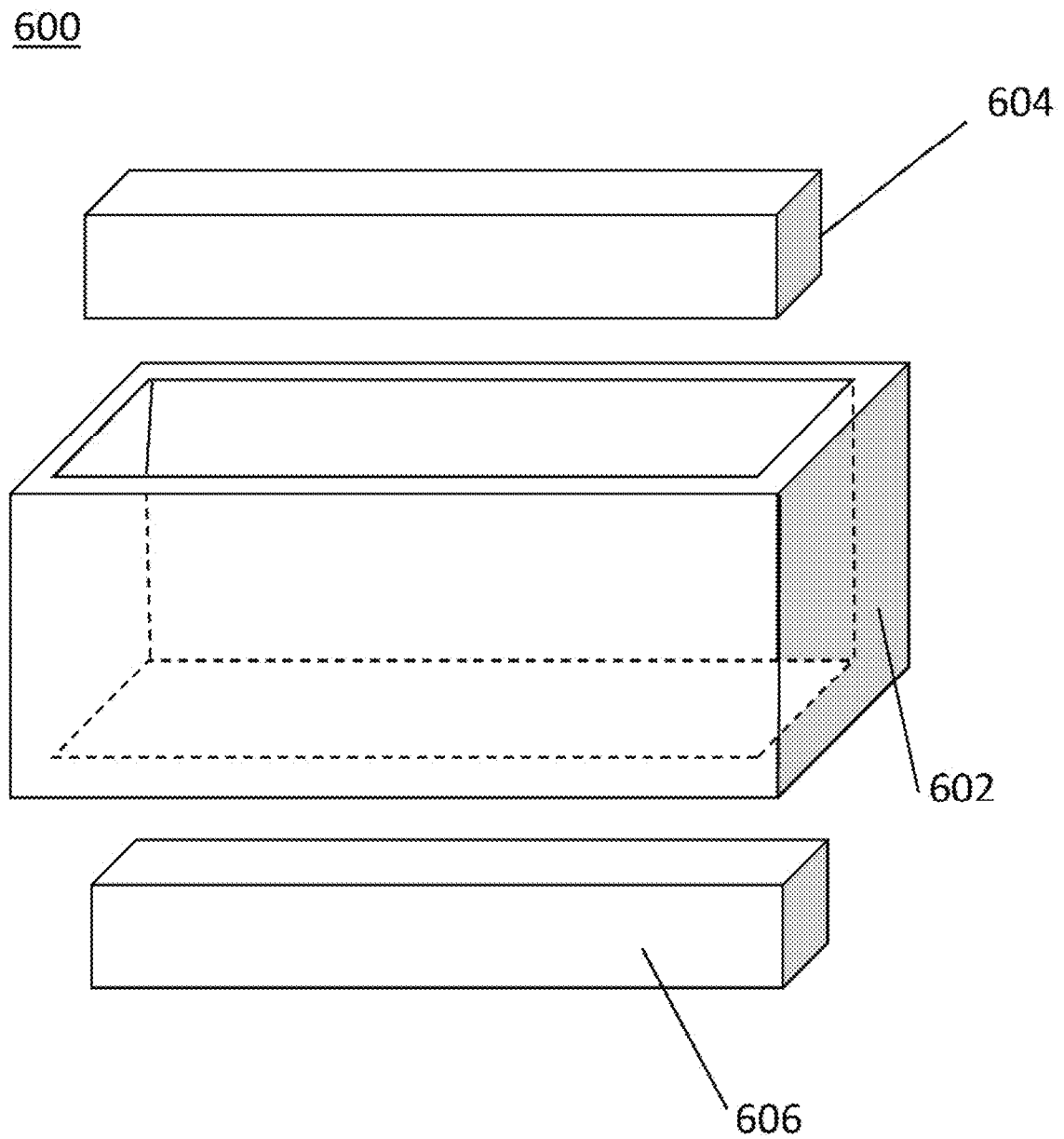
FIG. 6 is an illustration of puck mould designed to be used in conjunction with the rosin press according to various embodiments of the present invention.

An additional benefit of the rosin press 100 is that in using the rocker arm 112 and controller, a user has precise control of the height or distance separating the male and female plates. For example, this allows for placement of a puck mould between the plates. A non-limiting example of such a puck mould 600 is illustrated in FIG. 6. The puck mould 600 includes a frame 602 and a top press 604 and bottom press 606 that are designed to fit within a recess of the frame 602. During operation, plant material may be placed within the recess and between the top press 605 and bottom press 606. The mould 600 is then placed in the rosin press 100 and between the flat male and female plates (shown as elements 300 and 302 in FIG. 3). The plant material can then be easily compressed into a brick-like solid piece, otherwise known as a puck, doubling the amount of material to be pressed in a single rosin press. By choosing to compress the plant material prior to heat pressing the puck (i.e., between the plates), the amount of plant material able to be used in the rosin press is dramatically increased (e.g., doubled), thereby cutting down on usage time. Therefore, the ability of the rocker arm to raise high enough to allow the application of the puck mould essentially eliminates the need of a second press to make the pucks.

Figure 8A:
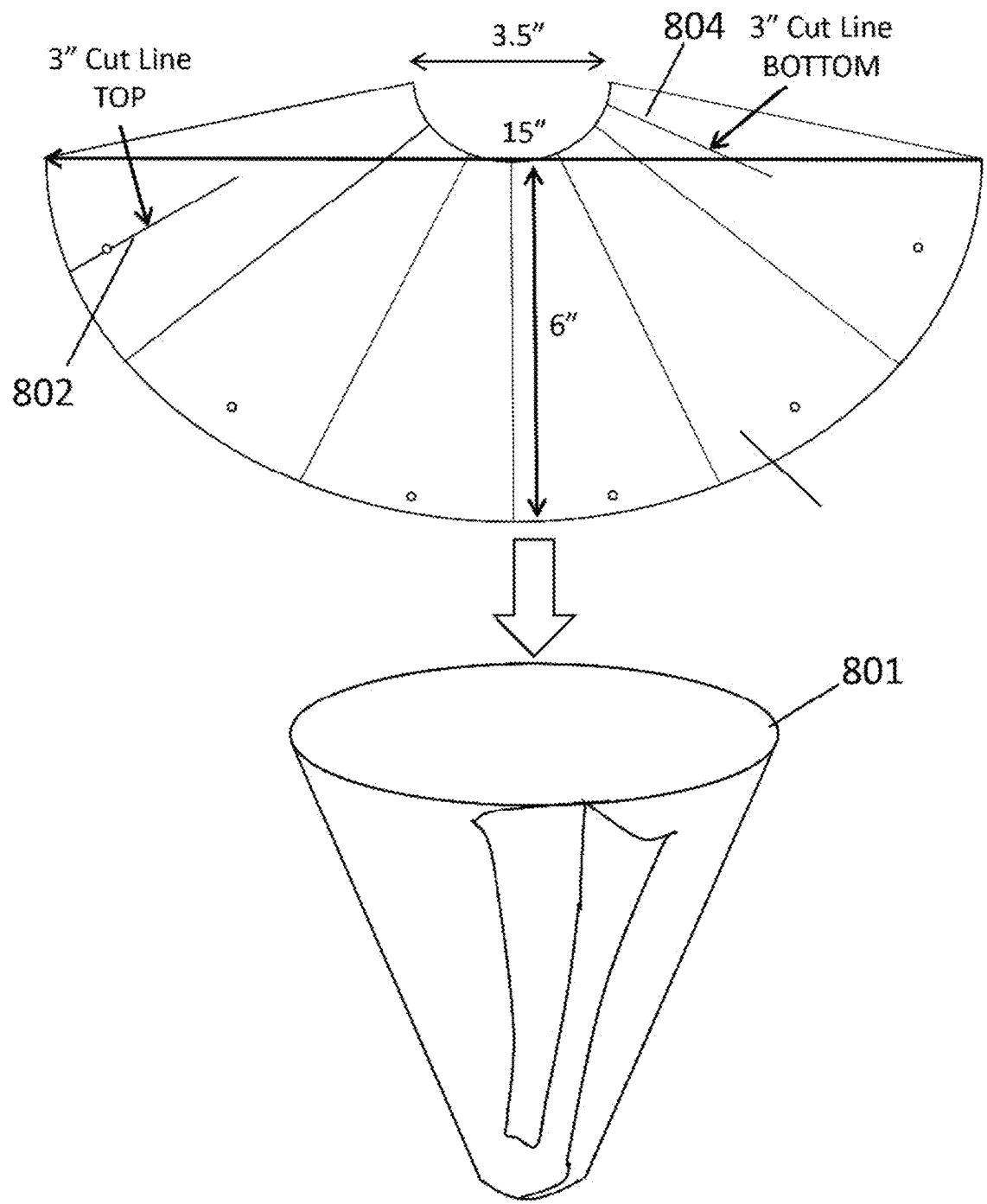
FIG. 8A is a schematic illustration of example shape and dimensions of a parchment cone according to various embodiments of the present invention as could be used with and designed to fit inside the male and female cone-shaped plates.

To assist in pressing the plant material and maintain a clean working surface, the invention described herein also includes parchment cones and mesh bags (e.g., micron mesh bags). The parchment cones are formed in any suitable manner and of any suitable material to be fit within and/or between the cone-shaped male and female plates. A non-limiting example of such a parchment cone 801 is seen in FIG. 8A. As a non-limiting example, the parchment cone 801 is depicted as being formed from a flat piece of parchment paper 800, with desirable dimensions and cut lines, so that the piece of parchment paper 800 folds into a cone shape. Although specific dimensions and cut lines are depicted, it should be understood that the invention is not intended to be limited thereto.

Figure 8B:
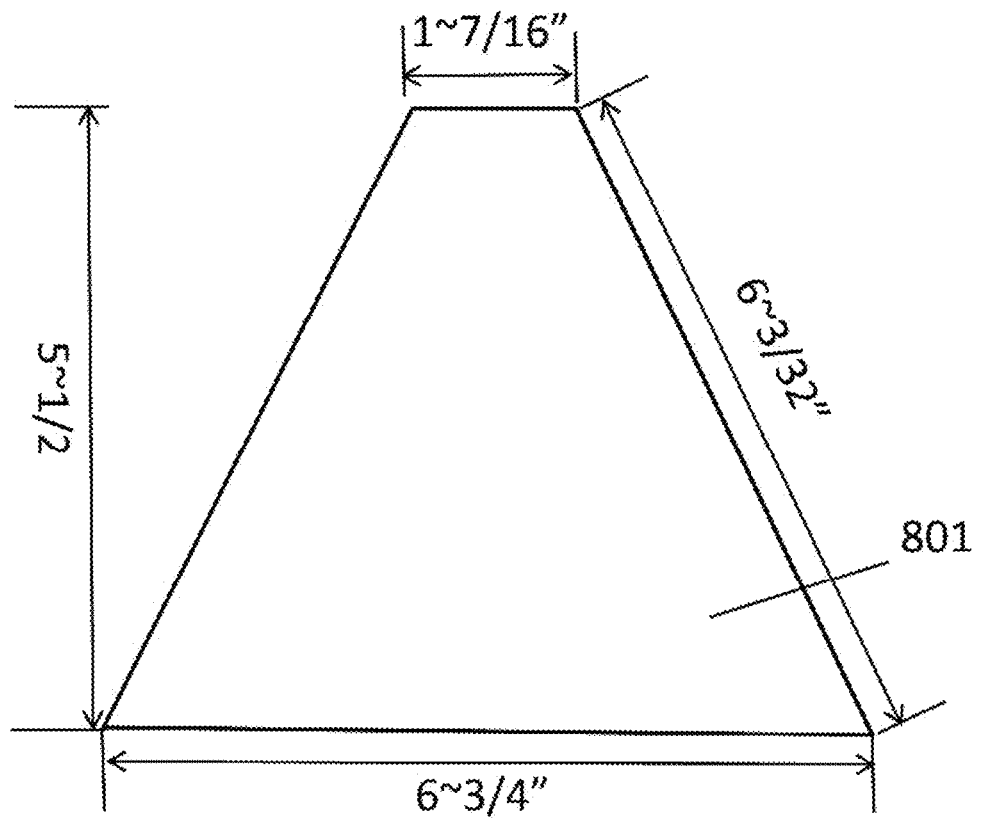
FIG. 8B is a schematic illustration of the parchment cone as shown in FIG. 8A, depicting the parchment cone in a rolled configuration to form a truncated cone shape, including example dimensions based off of those as detailed in FIG. 8A.

The parchment cone 801 can be developed and cut from a piece of standard parchment paper 801 in order to match the dimensions of the male and female cone-shaped plates. In other words, after formed or otherwise cut into such a shape, the parchment paper 800 can be easily rolled or manipulated into a cone-shape, thereby forming the parchment cone 801. In doing so, the top and bottom cut lines 802 and 804 can be slid within one another to affix the parchment paper 800 in the parchment cone 801 shape. As noted above, once the parchment paper 801 is cut, the parchment paper 801 can then be rolled into the truncated cone shape as indicated in FIG. 8B. As a non-limiting example, FIG. 8B illustrates a possible set of dimensions once the paper is rolled into the cone-shaped parchment cone 801.

The parchment cone 801 can be positioned onto the cone-shaped female plate to allow the rosin to escape onto the parchment cone 801 and not onto the cone-shaped plates themselves. This allows for less post-use cleaning, as the parchment cones 801 are removable. The parchment cone 801 can contain a male or female fitting, or can be formed of any suitable material, or be treated with other materials, such as Teflon coated, etc.

Figure 9:
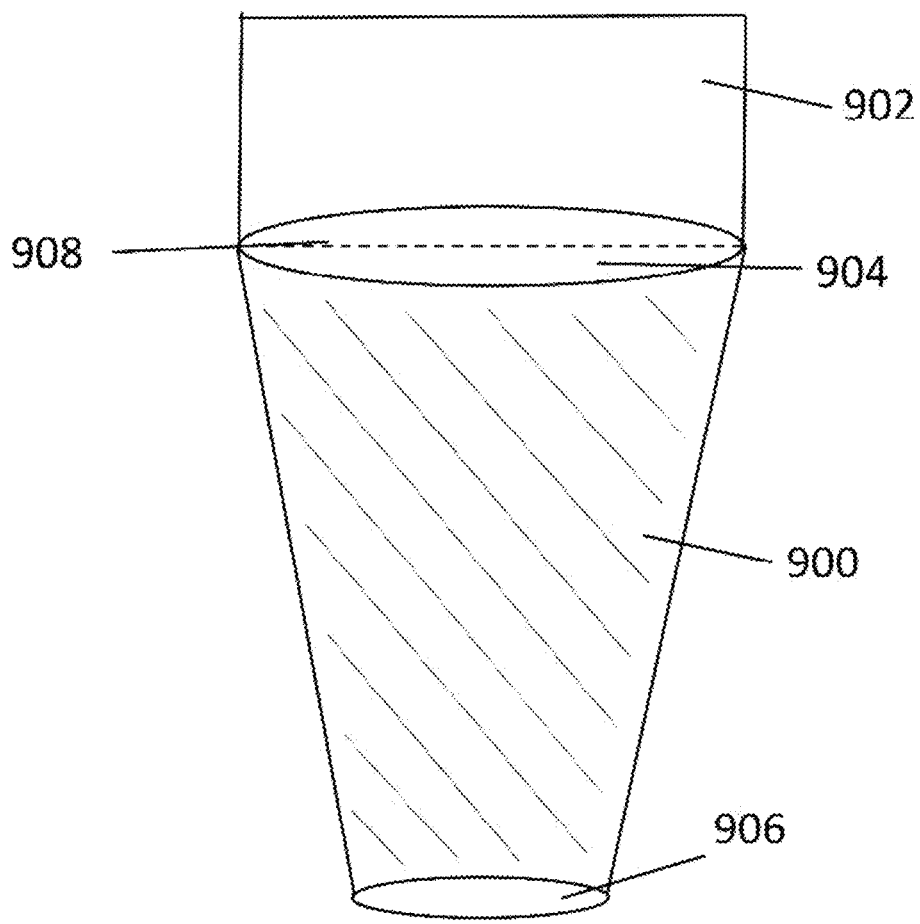
FIG. 9 is an illustration of a micron mesh bag according to various embodiments of the present invention, showing the mesh bag in its truncated cone shape with an extra flap of material as used to secure the bag to an outside of the female cone-shaped plate, as well as a hanging line for use when placing the mesh bag on the female cone-shaped plate.

The mesh bags, as mentioned before, are designed as a truncated cone in order to match the dimensions of the cone-shaped female plate, with enough space in between each mesh bag to allow the rosin a space to travel down between the bags as it progresses to the bottom of the female cone-shaped plate. In other words, the present invention also includes mesh bags that can be positioned around an interior of the cone-shaped female plate. For example, due to the truncated cone shape of each mesh bag, six or eight bags (or any other desired number depending on the dimensions and shape) can be fit side-by-side within the cone-shaped female plate. As shown in FIG. 9, the mesh bags 900 have an extra section of material 902 at the top so that they may fold over the top portion of the cone-shaped female plate, and be secured in place with a magnet or other fixture, such as a cone ring locking device. In addition and in some embodiments, the mesh bags 900 have an opening at the top 904 to allow the plant material to be placed inside, and an opening at the bottom 906 to allow the rosin to seep more easily from the bottom of the bag. The mesh bags 900 can be made of nylon material or any other desired material, they can be a "V" shaped bag (e.g., 6" tall by 2" wide) in another aspect, and can be formed to have micron holes between 25 microns to 220 microns (or any other desired dimension).

Figure 10A:
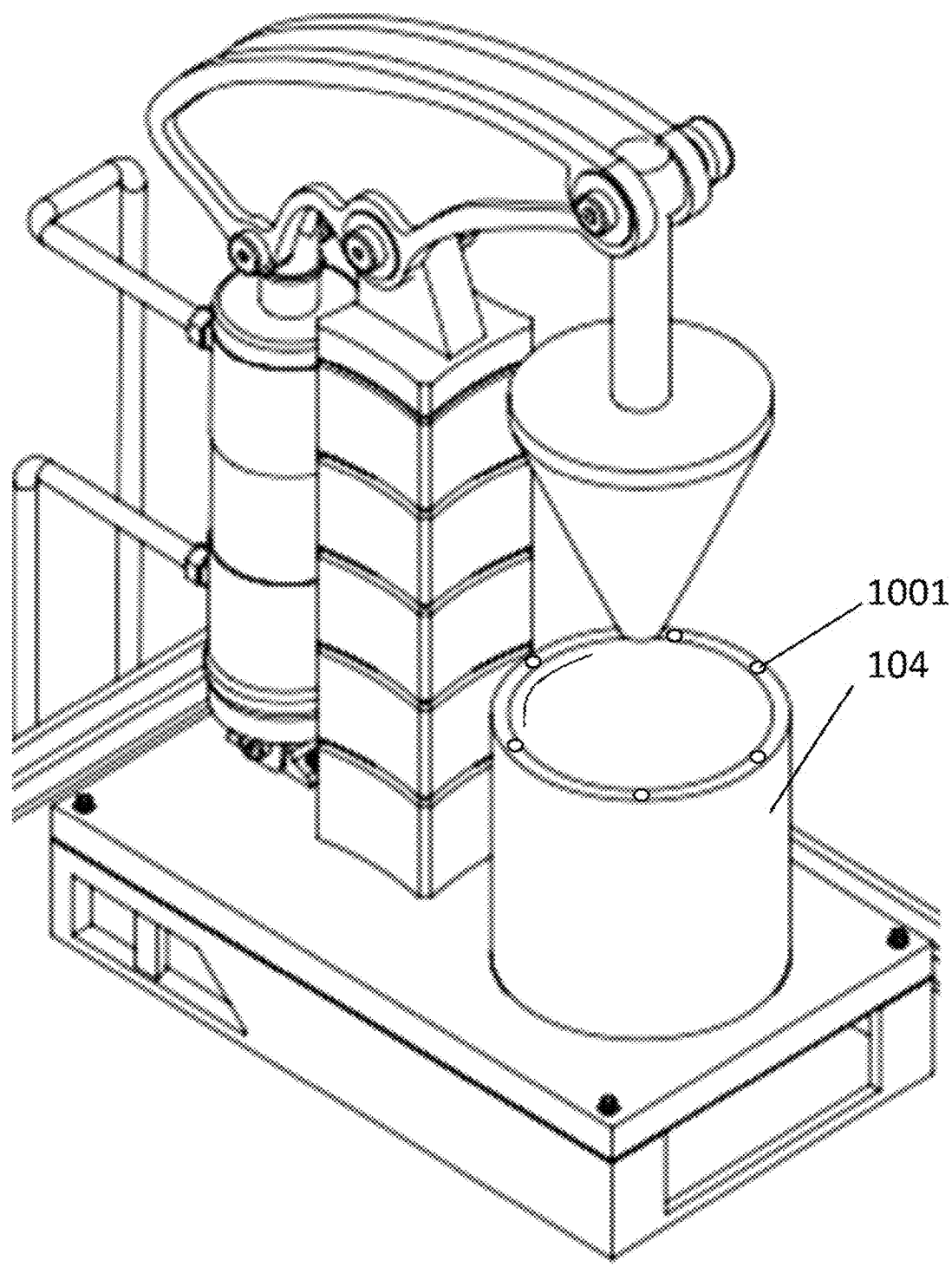
FIG. 10A is an illustration of the rosin press, depicting magnets positioned on the cone-shaped female plate.
Figure 10B:
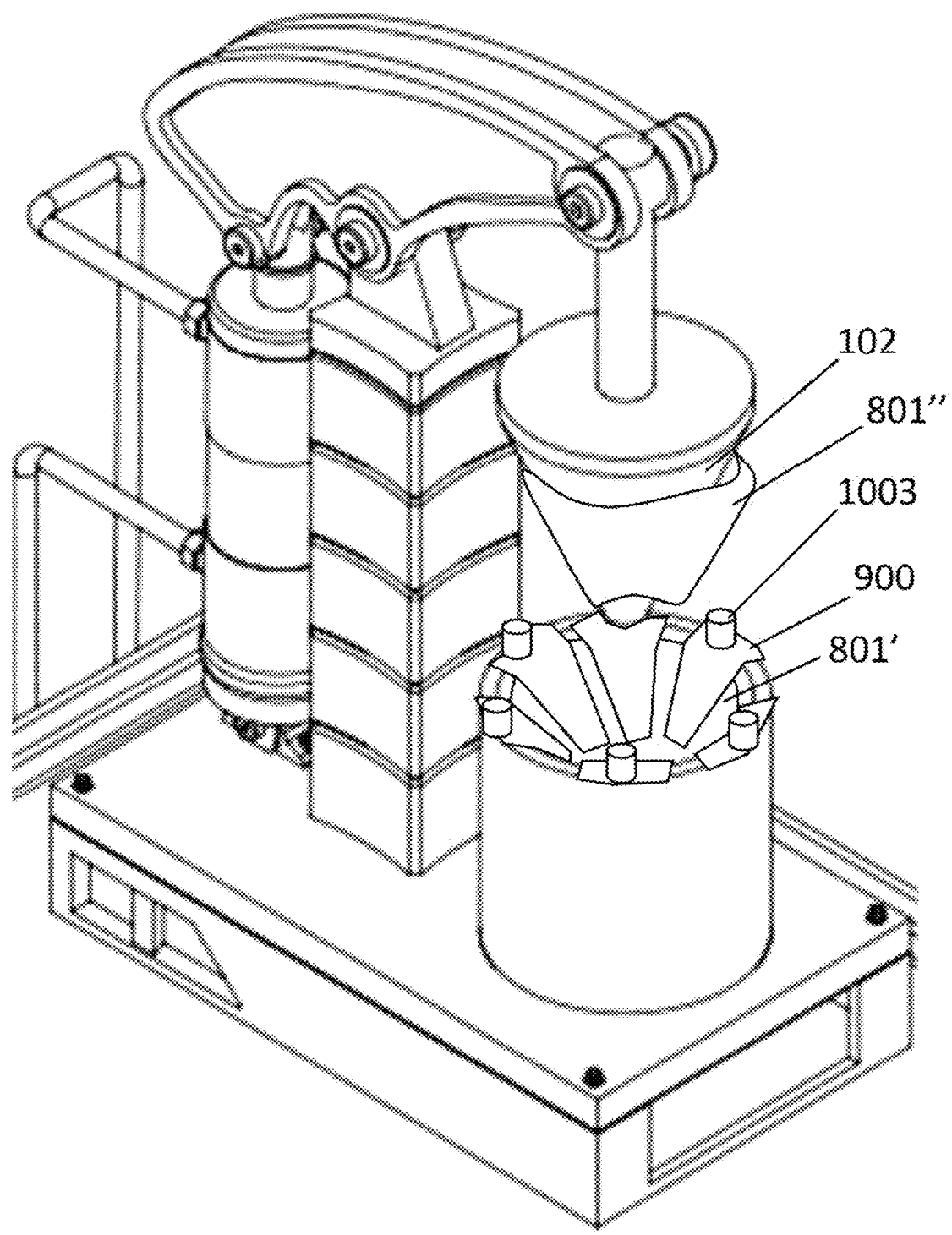
FIG. 10B is an illustration of the rosin press, depicting a parchment cone and a plurality of mesh bags positioned within the cone-shaped female plate.

As shown in FIG. 10A, any suitable fixture, device, or configuration can be used to assist in affixing the mesh bags with the cone-shaped female plate 104. As a non-limiting example, a plurality of magnets 1001 may be press fit into a lip on the top of the female plate 104, or on a ring or male cone attachment. In this aspect and as shown in FIG. 10B, a first parchment cone 801' can be positioned within female plate 104 with the plurality of mesh bags 900 laid over the parchment cone 801. Also shown are magnets 1003 that are used to affix the bags 900 with the female cone 104 (via magnetic attraction to the corresponding magnets positioned within the lip of the female plate 104. A second parchment cone 801" can then be positioned over the mesh bags 900 to sandwich the mesh, bags 900 between the first and second parchment cones 801' and 801". The male plate 102 is then pressed into the second parchment cone 801" which compresses the plant material therebetween.

Figure 10C:
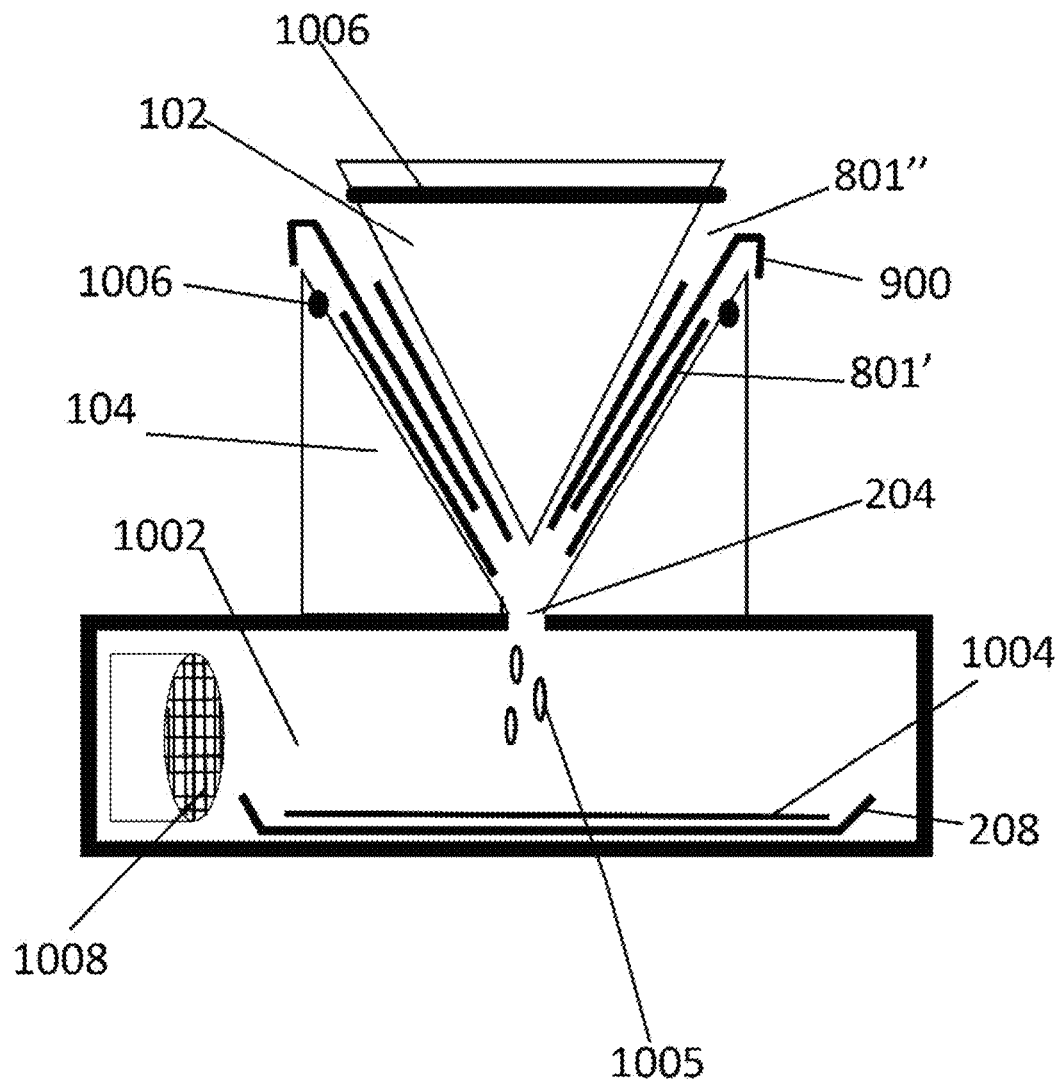
FIG. 10C is a cross-sectional, side-view illustration depicting placement of the mesh bags and the parchment cones between the cone-shaped male and female plates, and a corresponding post extraction cooling chamber.

The placement of the bags 900 and the parchment cones 801' and 801" can be seen in greater detail in the cross-sectional schematic shown in FIG. 10C. The male and female parchment cones 801' and 801" are separated by a plurality of mesh bags 900 containing plant material, and are placed so that they are trapped in-between the cone-shaped male 102 and female 104 plates. As the pressure begins to extract the rosin 1005 from the plant material, the rosin 1005 drips through the drain hole 204 in the bottom of the cone-shaped female plate 104 and into a plate, pan, or other collection item (such as tray or drawer 208). In various embodiments, the rosin 1005 falls into an oil cooling area 1002 where the tray or drawer 208 holds parchment paper 1004 or some other collection material. Once in the cooling area 1002, the rosin 1005 is naturally cooled and can be further cooled via air flow from a fan 1008.

In various embodiments and in order to prevent the rosin 1005 from seeping through the top gap between the cone-shaped male 102 and female 104 plates, a stopping mechanism (such as an O-ring 1006) is placed in the area where the plates 102 and 104 meet. In various embodiments, the O-ring 1006 is positioned around a top portion of the male plate 102. However, desirably, the O-ring 1006 is positioned within the female plate 104 (or in other embodiments, an O-ring 1006 can be positioned on both plates in an interlocking fashion). As a non-limiting example, a groove can be cut or otherwise formed within the female plate 104 a small distance (e.g., 0.25 inches, etc.) from the top of the female plate 104, with the O-ring 1006 positioned within the groove to wrap around an interior surface of the female plate 104. The O-ring 1006 serves multiple purposes, including locking the mesh bag 900 and the parchment cones 801' and 801" together to allow the oil or rosin 1005 to only flow towards the direction of the drain hole 204. The O-rings 1006 prevent the oil or rosin 1005 from spreading out the top in case the mesh bags 900 are placed too high and also prevent the oil from being caught in the extra mesh of the bags 900. The O-ring 1006 also provides a marked point for a user to place the mesh bags 900 when assembling by positioning the mesh bag 900 such that the plant material is below the O-ring 1006 line.

The rocker arms 112, as shown in FIG. 1 and discussed previously, also provide considerable benefit over the prior art. For example, while a single rocker arm can be used, multiple (e.g., two or more) rocker arms can also be included to provide additional pressure (e.g., double the amount of pressure) to the plates, which extracts the rosin at an increased rate (e.g., twice as fast), releasing the oil or rosin from the heat to give a solid yellow oil rosin and not a burnt or browned oil or rosin (which could occur if the rosin escapes slowly, as it is heated by the heated plates). While other presses may have high pressure, they do not have enough pressure to force out the rosin or oil quickly. Instead, prior art presses do not have sufficient amount of pressure which requires that the plates be held down longer on the plant material, resulting in a lesser quality (darker) oil being extracted.

In this aspect and as shown in FIG. 1, the dual rockers 116 are attached together and straddle the plate stem 122 and/or ram arm 130. A riser 132 or post includes a pivot bracket 134 through which a bolt or other fixture can be used to affix the rockers 116 with the riser 132 and provide an elevated pivot point 702. Thus, in pivoting about the pivot point 702, the dual rockers 116 provide double the pressure and also provide a space between them to run lines to heating elements and controllers.

Figure 7A:
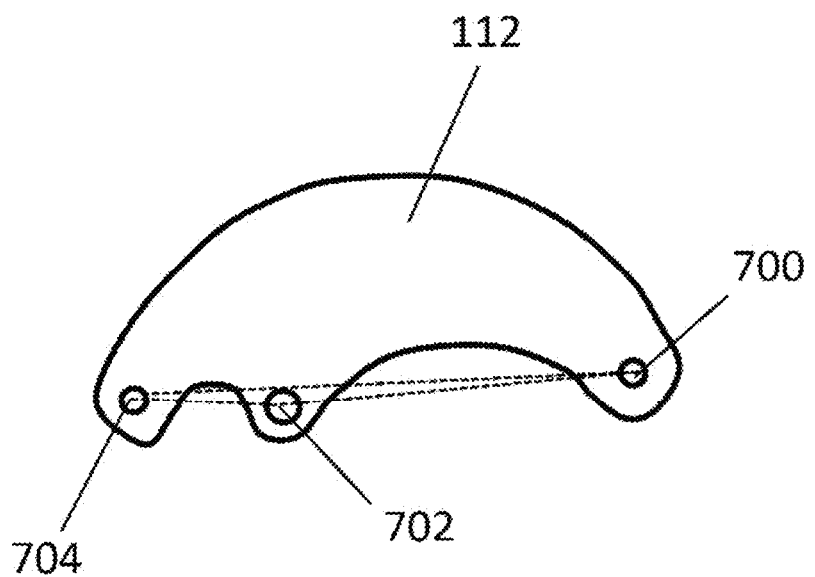
FIG. 7A is an illustration of a rocket arm according to various embodiments of the present invention, and the desirable placement relations between a pivot point and a ram bolt and stem bolt.

While the rocker arms 112 can be formed in any shape, in some embodiments, they have a curve or peak across their top as depicted. As seen in FIG. 7A, the curve or peak across the top directs pressure over and down so that the pressure put onto the press is directed down the plate stem toward the exact center of the plate, putting pressure from the center outwards in the plates to allow the oil to go from center to outside of plates. This assists the press in shooting out the oil from the plates with the right amount of heat.

Figure 7B:
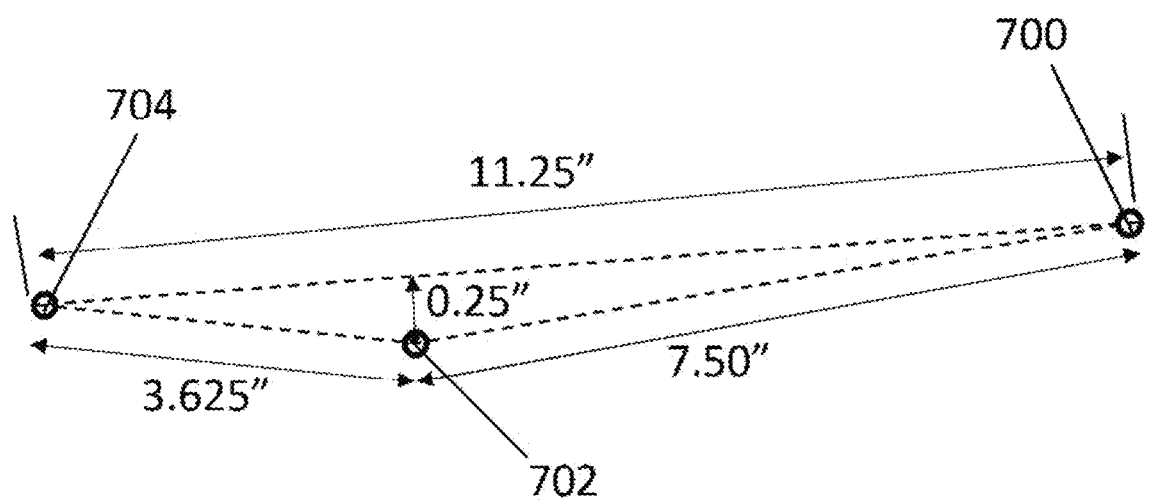
FIG. 7B is a further schematic illustration of dimensions of the rocker arm, detailing an example set of dimensions to achieve desired spacing between the pivot point, the ram bolt and the stem bolt.

Also, as shown, the distance between the stem bolt hole 700 and pivot point 702 can be any desired distance, and the distance between the ram bolt hole 704 and pivot point 702 can be any desired distance. However, as a non-limiting example and as depicted in FIG. 7B, the aforementioned distances are approximately 7.5 inches and 3.625 inches, respectively. Desirably, the distance between the stem bolt hole 700 and pivot point 702 is greater than the distance between the ram bolt hole 704 and pivot point 702. Although not limited thereto, the distance between the stem bolt hole 700 and pivot point 702 is approximately twice the distance between the ram bolt hole 704 and pivot point 702. This configuration allows for a considerable amount of pressure directed down the plate stem toward the male plate.

Also and as shown in FIG. 7A, an inverted triangle is formed by lines passing through the ram bolt hole 704 to the stem bolt hole 700 to the pivot point 702 to the ram bolt hole 704. This configuration allows the ram arm to fully extend without breaking the plate as the ram arm pushes the plate stem downward, giving a little extra pressure between the plates without breaking the plates.

Furthermore, another benefit of the rocker arms 112 design is that it creates the maximum amount of pressure directed to the rosin plate. The design of the rocker arms 112 allows an even pressure distribution along any size plate, thereby defeating the need to purchase different rosin presses to accommodate different size plates. For example and as noted above, the cone-shaped plates can be swapped out with a flat press and puck mould, or other item. As previously described, using a puck mould is beneficial because it doubles the amount of plant material and maximizes the resin and/or oil opportunity.

Figure 11A:
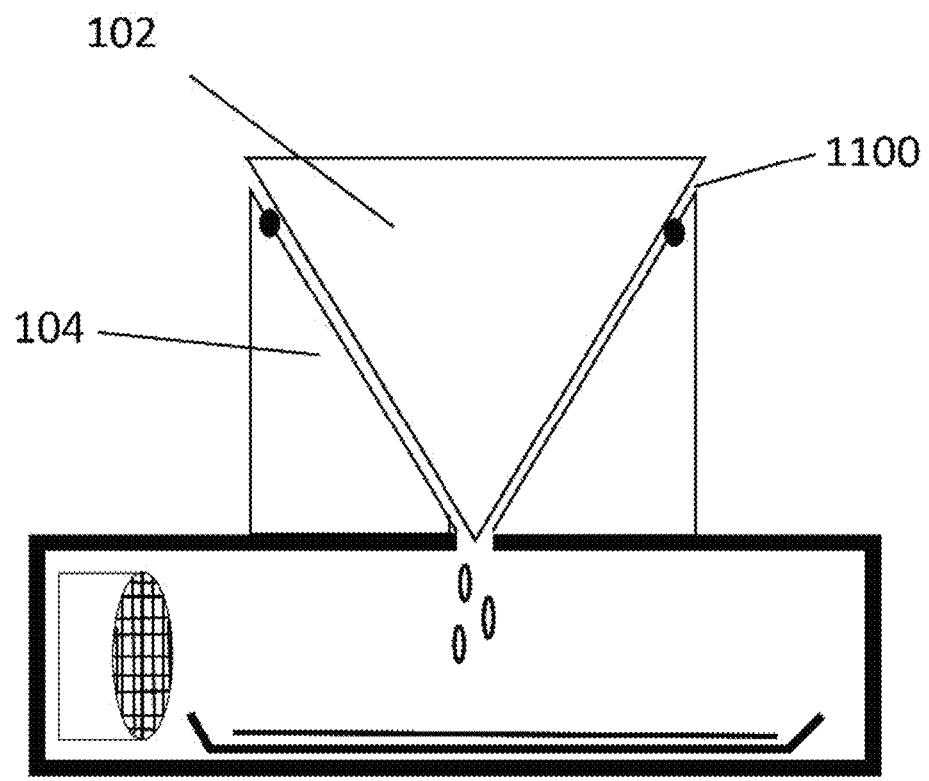
FIG. 11A is a cross-sectional, side-view illustration depicting cone-shaped male and female plates according to various embodiments of the present invention.
Figure 11B:
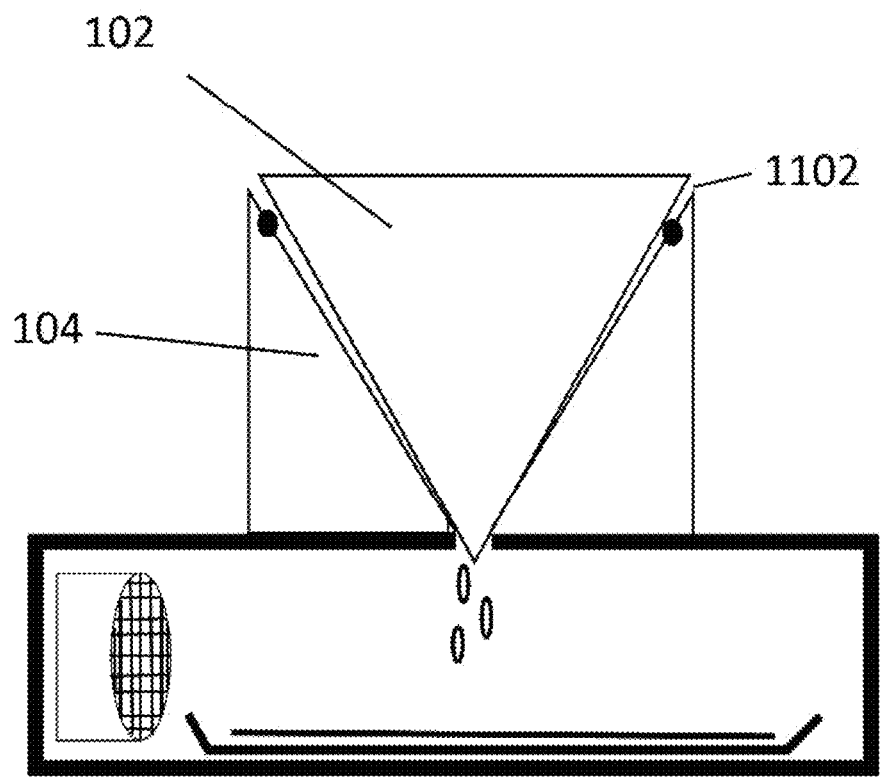
FIG. 11B is a cross-sectional, side-view illustration depicting cone-shaped male and female plates according to various embodiments of the present invention.
Figure 11C:
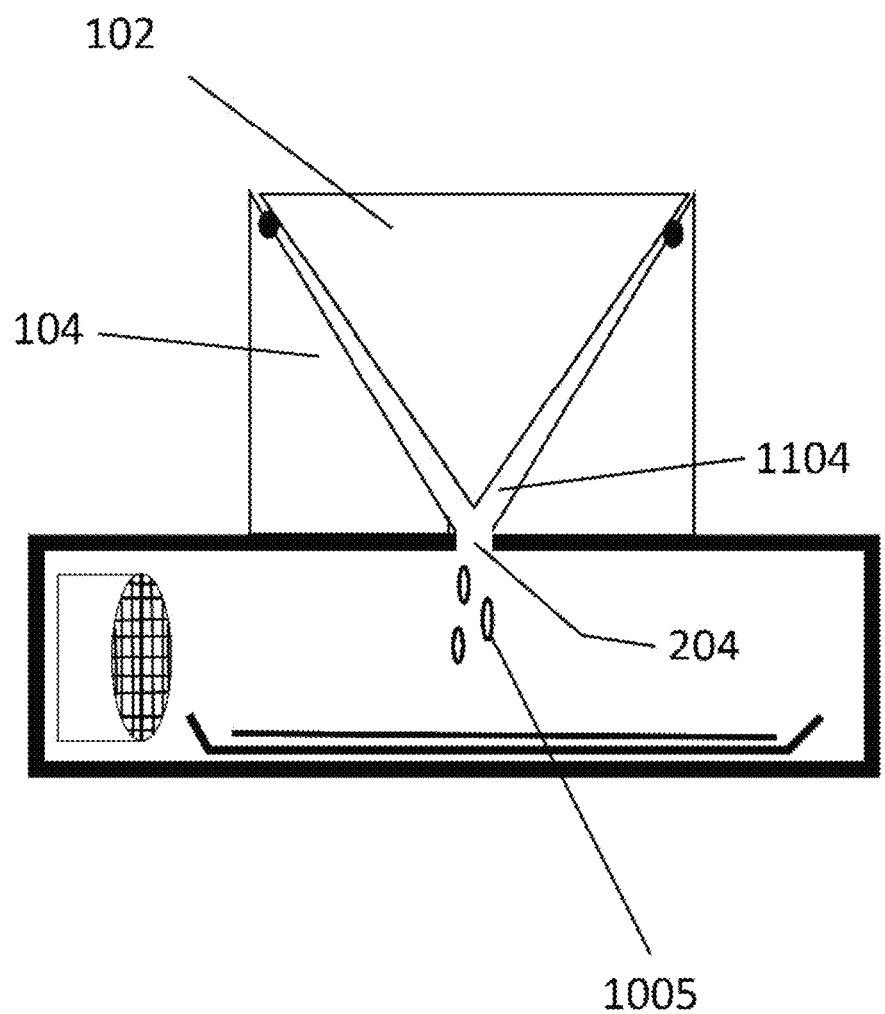
FIG. 11C is a cross-sectional, side-view illustration depicting cone-shaped male and female plates according to various embodiments of the present invention.

As can be appreciated by those skilled in the art, additional features can be added to this invention. For example, the heating element and the cone-shaped plates can be altered a number of ways. The cone-shaped plates can be manufactured to contain grooves to lock in the bags during pressing. The grooves would assist in controlling the directional flow of the oil as its extracted. Gutter runs can also be included that run toward the bottom of each plate for the oil to fall into for a faster escape route. The cone-shaped plates themselves can be larger or have a steeper angle, and the angle of the male and female plates can be matching or be changed with respect to one another. For example and as depicted in FIG. 11A, the angles of the male 102 and female 104 plates can be formed to match one another such that when a material (e.g., plant material) is positioned between the plates to form a small gap, the gap 1100 between the plates is consistent along a length of the plate faces. As another example and as depicted in FIG. 11B, the angles of the male 102 and female 104 plates can be formed such that a large gap 1102 exists between the walls at the top of the plates but is decreased toward the bottom of the plates where the plates would be driven toward touching one another. However, desirably and as shown in FIG. 11C, the angles of the male 102 and female 104 plates can be formed such that a larger gap 1104 exists toward the bottom of the plates but is minimized or decreased toward the top of the plates, to allow for increased pressure on the material. Such a configuration allows for increasing pressure to be applied to the plant material while driving the rosin from the plant material and toward the drain hole 204. While the angle of the male plate 102 is depicted as being consistent along its length, it can also be formed such that the angle changes slightly such that when the plates 102 and 104 are pressed together, a middle portion of the plates 102 and 104 would touch with a gap 1104 being formed toward the bottom of the plates 102 and 104.

Figure 11D:
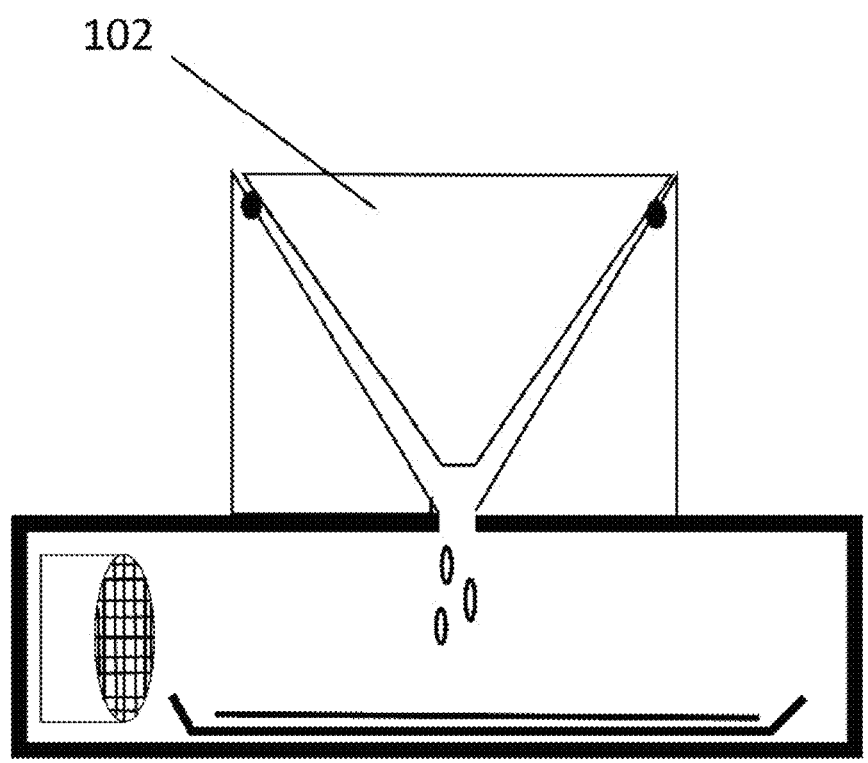
FIG. 11D is a cross-sectional, side-view illustration depicting cone-shaped male plate according to various embodiments of the present invention.

It should be noted that although the male plate 102 is depicted as ending in a tip, it is not intended to be limited thereto. For example, desirably, the male plate 102 is formed such that the tip is flattened out, forming a truncated or frustum shape, as shown in FIG. 11D. It should be also understood that any of the features and various aspects as described herein can be interchanged with one another as feasible and desired. As a non-limiting example, the truncated cone of the male plate 102 shown in FIG. 11D can be implemented in all versions as described and illustrated.

In yet other aspects, the heating elements can be placed in different locations and be altered in number or design. Further, the pressure driving element can be altered as well as desired. For example, the ram can be upgraded to 21,0000 psi (or any other suitable configuration), or have additional rams or different mounting brackets. The ram and/or rocker arms can also be bigger or be angled differently, or otherwise be modified or altered as desired.

Thus, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:
1. A rosin press system, comprising:
a first male plate;
a first female plate having a recess formed therein to matingly receive the first male plate; and
wherein a first pair of heating elements is embedded within the first male plate and a second pair of heating elements is embedded within the first female plate;
wherein the first male plate is a cone-shaped male plate and the first female plate is a cone-shaped female plate;
wherein the cone-shaped female plate has a centrally positioned drain hole;
wherein the cone-shaped male plate includes a stem rising from a top portion of the cone-shaped male plate;
further comprising a parchment cone, the parchment cone formed of planar parchment paper having at least two cut lines therein, such that upon rolling and affixing the cut lines, the parchment paper is maintained as a parchment cone;
further comprising a mesh bag, the mesh bag having a truncated cone shape, wherein the mesh bag includes an open top portion and an open bottom portion, with the top portion being wider than the bottom portion, and further comprising a flap extending from the open top portion;
further comprising an O-ring positioned within the cone-shaped female plate;
further comprising a flat male plate having a stem protruding therefrom, the flat male plate being interchangeable with the cone-shaped male plate;
further comprising a flat female plate, the flat female plate being formed to nest within a top portion of the cone-shaped female plate;
further comprising a plurality of magnets attached with a top portion of the cone- shaped female plate;
wherein the cone-shaped male plate has a truncated tip;
wherein when the cone-shaped male plate is pressed into the cone-shaped female plate, a gap exists between the cone-shaped male and female plates proximate the drain hole;
further comprising:
a base supporting the cone-shaped female plate;
a riser attached with the base;
a pair of rocker arms pivotally attached with the riser about a pivot point, the rocker arms having a ram bolt hole and a stem bolt hole, wherein the stem of the cone-shaped male plate is pivotally connected with the stem bolt hole; and
a ram attached with the base, the ram having a ram arm connected with the ram bolt hole, whereby causing the ram arm to raise forces the pair of rocker arms to pivot about the pivot point and press the cone-shaped male plate into the cone-shaped female plate.

* * * * *